United States Patent [19]

Cooper et al.

[11] Patent Number: 5,276,050

[45] Date of Patent: Jan. 4, 1994

[54] MEDICAMENTS

[75] Inventors: Steven J. Cooper, Birmingham; Ian H. Coates, Hertford; Alexander W. Oxford; Peter C. North, both of Royston, all of England

[73] Assignee: Glaxo Group Limited, London, England

[21] Appl. No.: 908,329

[22] Filed: Jul. 6, 1992

Related U.S. Application Data

[63] Continuation of Ser. No. 723,265, Jun. 28, 1991, abandoned, which is a continuation of Ser. No. 560,758, Jul. 31, 1990, abandoned.

[30] Foreign Application Priority Data

Aug. 1, 1989 [GB] United Kingdom ............... 8917557

[51] Int. Cl.$^5$ .......................................... A61K 31/415
[52] U.S. Cl. ..................................................... 514/397
[58] Field of Search ........................................ 514/397

[56] References Cited

FOREIGN PATENT DOCUMENTS

| | | |
|---|---|---|
| 0357414A2 | 3/1990 | European Pat. Off. . |
| 0357415A2 | 3/1990 | European Pat. Off. . |
| 0357416A2 | 3/1990 | European Pat. Off. . |
| 2625678 | 7/1989 | France . |
| WO90/12569 | 11/1990 | PCT Int'l Appl. . |
| 2153821B | 1/1988 | United Kingdom . |
| 2206788A | 1/1989 | United Kingdom . |
| 2209335A | 5/1989 | United Kingdom . |

OTHER PUBLICATIONS

Ven der Hoek et al., *J. Psychopharmacol.*, 4(4), 1990, 288 (Abstract for the British Association for Psychopharmacology Annual Meeting, Cambridge, Jul. 1990).
*The Lancet*, Mar. 19, 1988, p. 629.
Cooper, *TIPS*, Feb. 1989, vol. 10, pp. 56–57.

*Primary Examiner*—S. J. Friedman
*Attorney, Agent, or Firm*—Bacon & Thomas

[57] ABSTRACT

The invention relates to the use of compounds of the general formula (I)

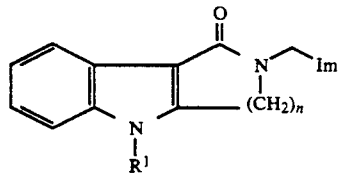

and physiologically acceptable salts and solvates thereof, in which Im represents an imidazolyl group of formula:

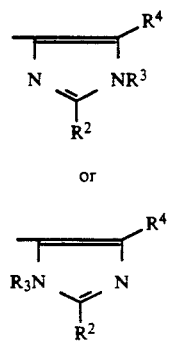

and $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl, phenyl$C_{1-3}$alkyl, phenylmethoxymethyl, phenoxyethyl, phenoxymethyl, —$CO_2R^5$, —$COR^5$, —$CONR^5R^6$ or —$SO_2R^5$ (wherein $R^5$ and $R^6$, which may be the same or different each represents a hydrogen atom, a $C_{1-6}$alkyl or $C_{3-7}$cycloalkyl group, or a phenyl or phenyl$C_{1-4}$alkyl group, in which the phenyl group is optionally substituted by one or more $C_{1-4}$alkyl, $C_{1-4}$alkoxy or hydroxy groups or halogen atoms, with the proviso that $R^5$ does not represent a hydrogen atom when $R^1$ represents a group —$CO_2R^5$ or —$SO_2R^5$);

one of the groups represented by $R^2$, $R^3$ and $R^4$ is a (Abstract continued on next page.)

hydrogen atom or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$alkyl group;

and n represents 2 or 3, for the treatment of a condition involving excessive eating, for example bulimia.

11 Claims, No Drawings

MEDICAMENTS

This application is a continuation of application Ser. No. 07/723,265, filed Jun. 28, 1991, which is a continuation of application Ser. No. 07/560,758, filed Jul. 31, 1990, both now abandoned.

This invention relates to a new medical use for a group of heterocyclic compounds and pharmaceutical compositions containing them. In particular it relates to the use of certain lactam derivatives in the treatment of conditions involving excessive eating.

French Patent Specification No. 2625678 discloses the use of various quinuclidine benzamides and thiobenzamides, together with their N-oxides, hydrates and salts in the treatment of increased weight and obesity of various causes. The use of 4-amino-5-chloro-2-methoxy-N-(quinuclidin-3-yl)benzamide (which has the approved name zacopride), a compound which is known to be an antagonist of 5-hydroxytryptamine (5-HT) at 5-HT$_3$ receptors, is specifically described.

UK Patent Specification No. 2153821B discloses the use of various 1,2,3,9-tetrahydro-3-[(imidazol-1-yl)methyl]-4H-carbazol-4-ones and their salts and solvates in the treatment of inter alia obesity. UK2153821B describes these tetrahydrocarbazolones as potent and selective antagonists of 5-HT at 'neuronal' 5-HT receptors of the type located on terminals of primary afferent nerves, receptors of this type now being designated as 5-HT$_3$ receptors.

U.K. Patent Specification No. 2209335A discloses compounds of the general formula (I):

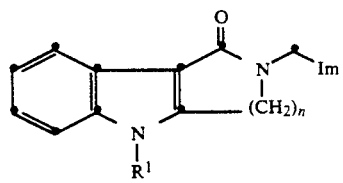

(I)

In the above formula Im represents an imidazolyl group of formula:

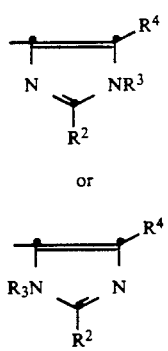

and R$^1$ represents a hydrogen atom or a group selected from C$_{1-6}$alkyl, C$_{3-6}$alkenyl, C$_{3-10}$alkynyl, C$_{3-7}$cycloalkyl, C$_{3-7}$cycloalkylC$_{1-4}$ alkyl, phenyl, phenylC$_{1-3}$alkyl, phenylmethoxymethyl, phenoxyethyl, phenoxymethyl, —CO$_2$R$^5$, —COR$^5$, —CONR$^5$R$^6$ or —SO$_2$R$^5$ (wherein R$^5$ and R$^6$, which may be the same or different, each represents a hydrogen atom, a C$_{1-6}$ alkyl or C$_{3-7}$ cycloalkyl group, or a phenyl or phenylC$_{1-4}$alkyl group, in which the phenyl group is optionally substituted by one or more C$_{1-4}$ alkyl, C$_{1-4}$ alkoxy or hydroxy groups or halogen atoms, with the proviso that R$^5$ does not represent a hydrogen atom when R$^1$ represents a group —CO$_2$R$^5$ or —SO$_2$R$^5$);

one of the groups represented by R$^2$, R$^3$ and R$^4$ is a hydrogen atom or a C$_{1-6}$alkyl, C$_{3-7}$cycloalkyl, C$_{3-6}$alkenyl, phenyl or phenylC$_{1-3}$alkyl group, and each of the other two groups, which may be the same or different, represents a hydrogen atom or a C$_{1-6}$ alkyl group;

and n represents 2 or 3.

Suitable physiologically acceptable salts of the compounds of general formula (I) include acid addition salts formed with organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates. The solvates may, for example, be hydrates.

The compounds of formula (I) are described in UK2209335A as potent and selective antagonists of 5-HT at 5-HT$_3$ receptors, and as being of use in the treatment of conditions such as anxiety, psychotic disorders (e.g. schizophrenia and mania); nausea and vomiting (particularly that associated with cancer chemotherapy and radiotherapy); gastric stasis; symptoms of gastrointestinal dysfunction such as dyspepsia, peptic ulcer, reflux oesophagitis, flatulence and irritable bowel syndrome; migraine; and pain. It is also stated that the compounds may be used in the treatment of dependency on drugs and substances of abuse, depression, and dementia and other cognitive disorders.

It has now been found that compounds which are antagonists of 5-HT at 5-HT$_3$ receptors, such as the compounds of formula (I), are useful for the treatment of conditions involving excessive eating, in particular bulimia. Bulimia (and more specifically bulimia nervosa) is a condition in which there is an abnormal desire for food, particularly rich, sweet, and highly palatable foods, which leads to over-indulgence and bouts of binge eating. This is combined with an overconcern for body size, such that excessive eating is often followed by purging and/or vomiting. The compounds of formula (I) are also useful for the treatment of other conditions which involve excessive eating, such as obesity and seasonal affective disorder (SAD).

The ability of 5-HT$_3$ receptor antagonists, such as the compounds of formula (I), to suppress the intake of palatable foods has been demonstrated in rats. Thus in rats familiarised with eating an enriched sweetened mash, administration of a 5-HT$_3$ receptor antagonist resulted in significant reductions in food intake.

Accordingly the invention provides a method of treatment of a subject suffering from bulimia or another condition involving excessive eating, which comprises administering to the subject an effective amount of a compound of formula (I) or a physiologically acceptable salt or solvate thereof.

References in this specification to treatment include prophylactic treatment as well as the acute alleviation of symptoms.

The use of all optical isomers of compounds of general formula (I) and their mixtures including the racemic mixtures thereof, and all the geometric isomers of compounds of formula (I), is embraced by the invention.

A preferred group of compounds of formula (I) for use according to the invention is that wherein $R^1$ represents a hydrogen atom or a $C_{1-4}$ alkyl, $C_{3-4}$alkenyl, $C_{3-4}$alkynyl, $C_{5-6}$cycloalkyl, $C_{5-6}$cycloalkylmethyl, phenyl$C_{1-2}$ alkyl, phenylmethoxymethyl, N,N-di$C_{1-3}$alkylcarboxamido or $C_{1-3}$alkylsulphonyl group; $R^2$ represents a hydrogen atom; and $R^3$ and $R^4$ each represent a hydrogen atom or a $C_{1-3}$ alkyl group.

A particularly preferred group of compounds of formula (I) for use according to the invention is that wherein $R^1$ represents a methyl, n-propyl, prop-2-ynyl, cyclopentyl, cyclopentylmethyl, benzyl or N,N-dimethylcarboxamido group; $R^2$ and $R^3$ each represent a hydrogen atom; and $R^4$ represents a methyl group.

Within the above preferred and particularly preferred groups of compounds, an especially important group of compounds is that in which n represents 2.

Another preferred group of compounds of formula (I) for use according to the invention is that wherein $R^1$ represents a hydrogen atom or a $C_{1-4}$alkyl (e.g. methyl, ethyl, n-propyl or isopropyl) group; $R^2$ and $R^3$ each represent a hydrogen atom; $R^4$ represents a methyl group; and n is 2.

A preferred compound for use according to the invention is: 2,3,4,5-tetrahydro-2-[(5-methyl-1H-imidazol-4-yl)methyl]-5-propyl-1H-pyrido[4,3-b]indol-1-one and its physiologically acceptable salts and solvates.

Other preferred compounds for use according to the invention are:
5-ethyl-2,3,4,5-tetrahydro-2-[(5-methyl-1H-imidazol-4-yl)methyl]-1H-pyrido[4,3-b]indol-1-one;
2,3,4,5-tetrahydro-5-(1-methylethyl)-2-[(5-methyl-1H-imidazol-4-yl)methyl]-1H-pyrido[4,3-b]indol-1-one;
2,3,4,5-tetrahydro-2-[(5-methyl-1H-imidazol-4-yl)methyl]-1H-pyrido[4,3-b]indol-1-one;
and their physiologically acceptable salts and solvates.

A particularly preferred compound for use according to the invention is 2,3,4,5-tetrahydro-5-methyl-2-[(5-methyl-1H-imidazol-4-yl)methyl]-1H-pyrido[4,3-b]indol-1-one and its physiologically acceptable salts and solvates. Preferred salts of this compound are the hydrochloride and maleate, of which the hydrochloride is particularly preferred.

In a further aspect, the invention provides a pharmaceutical composition which comprises an effective amount of a compound of formula (I) or a physiologically acceptable salt or solvate (e.g. hydrate) thereof, for use in medicine, particularly human medicine, for the treatment of bulimia or another condition involving excessive eating.

In a yet further aspect, the invention provides for the use of a compound of formula (I) or a physiologically acceptable salt or solvate thereof, for the manufacture of a medicament for the treatment of bulimia or another condition involving excessive eating.

Pharmaceutical compositions for use in accordance with the present invention may be formulated in conventional manner using one or more physiologically acceptable carriers or excipients.

Thus the compounds of formula (I) and their physiologically acceptable salts and solvates may be formulated for oral, buccal, parenteral, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (I) may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of formula (I) may also be formulated in rectal compositions such as suppositories or retention enemas, e.g. containing conventional suppository bases such as cocoa butter or other glycerides.

In addition to the formulations described previously, the compounds may also be formulated as depot preparations. Such long acting formulations may be administered by implantation (for example subcutaneously, transcutaneously or intramuscularly) or by intramuscular injection. Thus, for example, the compounds of formula (I) may be formulated with suitable polymeric or hydrophobic materials (for example as an emulsion in an acceptable oil) or ion exchange resins, or as sparingly soluble derivatives, for example, as a sparingly soluble salt., A proposed dose of a compound of formula (I) for use according to the invention for administration to a subject (of approximately 70 kg body weight) is 0.001 to 100 mg, for example 0.01 to 50 mg, more preferably 0.1 to 20 mg, of the active ingredient per unit dose, expressed as the weight of free base. The unit dose may be administered, for example, 1 to 4 times per day. The dose will depend on the route of administration. It will be appreciated that it may be necessary to make routine variations to the dosage depending on the age and weight of the patient as well as the severity of the condition to be treated.

Compounds of general formula (I) and physiologically acceptable salts or solvates thereof, may be prepared by the methods described in U.K. Patent Specification No. 2209335A.

The following examples illustrate the preparation of 2,3,4,5-tetrahydro-5-methyl-2-[(5-methyl-1H-imidazol-4-yl)methyl]-1H-pyrido[4,3-b]indol-1-one and its hydrochloride salt, covered by formula (I). Temperatures are in °C. Thin layer chromatograpy (t.l.c.) was carried out on silica.

EXAMPLE 1

2,3,4,5-Tetrahydro-5-methyl-2-[(5-methyl-1H-imidazol-4-yl)methyl]-1H-pyrido[4,3-b]indol-1-one.

A mixture of 2,3,4,5-tetrahydro-5-methyl-1H-pyrido[4,3-b]indol-1-one (49.97 g), p-toluenusulphonic acid monohydrate (9.50 g) and 4-hydroxymethyl-5-methylimidazole hydrochloride (20.25 g) in N-methylpyrrolidinone (250 ml) was stirred and heated to 125° (over 1 h) The reaction was then heated at 125°-130° for 4.5 h, during which time two further portions of 4-hydroxymethyl-5-methylimidazole hydrochloride (17.51 g and 6.88 g) were added. The reaction mixture was cooled, diluted with water (100 ml), and the stirred mixture was treated slowly with 8% aqueous sodium bicarbonate (750 ml). The resultant suspension was stirred in an ice bath for 1 h and then filtered to give a solid (57.64 g). A portion of this solid (11.09 g) was dissolved in dichloromethane (307 ml) and ethanol (166 ml), boiled with decolourising charcoal for 10 min and then filtered. The dichloromethane was distilled off at atmospheric pressure until the temperature of the mixture was at 65°. The stirred mixture was cooled and the resulting precipitate was filtered off to give the title compound (9.28 g), t.l.c. (dichloromethane: ethanol: 0.88 ammonia, 50:8:1) Rf 0.55.

$^1$H-n.m.r (DMSO-d$_6$): δ2.20(3H,s), 3.03(2H,t), 3.64(2H,m), 3.71(3H,s), 4.50(2H,s), 7.19(2H,m), 7.44(1H,s), 7.50(1H,d), 7.99(1H,d), 11.76(1H,s).

EXAMPLE 2

2,3,4,5-Tetrahydro-5-methyl-2-[(5-methyl-1H-imidazol-4-yl)methyl]-1H-pyrido[4,3-b]indol-1-one hydrochloride 2,3,4,5-Tetrahydro-5-methyl-2-[(5-methyl-1H-imidazol-4-yl)methyl]-1H-pyrido[4,3-b]indol-1-one (1.00 g) was suspended in ethanol (40 ml) and concentrated hydrochloric acid (1.00 ml) was added. The mixture was warmed to 40° and charcoal (0.25 g) was added. The resulting suspension was stirred and warmed for 5 min. and then filtered. The filtrate was evaporated in vacuo to ca. 20 ml and was allowed to cool to 20°. Ether (40 ml) was added with stirring over 5 min., and the mixture was stored at 4° overnight. The resulting precipitate was filtered off, washed with ether (2×10 ml), dried in vacuo at room temperature for 2 h and then at 70° for 7 h to give the title compound (0.95 g), m.p. 288°-291°.

Analysis Found: C,61.4; H,5.8; N,16.7; Cl,10.7; C$_{17}$H$_{18}$N$_4$O.HCl requires C,61.7; H,5.8; N,16.9; Cl,10.7%.

The following examples illustrate pharmaceutical formulations for use according to the invention, containing 2,3,4,5-tetrahydro-5-methyl-2-[(5-methyl-1H-imidazol-1-yl)methyl]-1H-pyrido[4,3-b]indol-1-one hydrochloride as the active ingredient. Other physiologically acceptable salts and/or solvates of this compound, and other compounds of formula (I) and their physiologically acceptable salts and/or solvates may be formulated in a similar manner.

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

| Tablet | Direct Compression mg/tablet |
|---|---|
| Active Ingredient | 0.562 |
| Microcystalline cellulose NF* | 31.250 |
| Lactose (anhydrous) NF | 111.303 |
| Pregelatinised maize starch BP | 6.250 |
| Magnesium Stearate | 0.625 |
| Compression weight | 150.0 |

*of a grade suitable for direct compression.

The active ingredient is passed through a 60 mesh sieve, blended with the lactose, microcystalline cellulose, pregelatinised maize starch and magnesium stearate. The resultant mix is compressed into tablets using a suitable tablet machine fitted with 7.0 mm, normal concave punches.

INJECTION FOR INTRAVENOUS ADMINISTRATION

| | mg/ml | |
|---|---|---|
| Active ingredient | 0.0562 | 0.562 |
| Sodium Chloride BP | as required | as required |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

SUPPOSITORY

| Active Ingredient | 0.562 mg |
|---|---|
| * Witepsol H15 to | 1.0 g |

* Witepsol H15 is a proprietary grade of Adeps Solidus Ph. Eur.

A suspension of the active ingredient is prepared in the molten Witepsol and filled, using suitable machinery, into 1 g size suppository moulds.

We claim:

1. A method for the treatment of bulimia or seasonal affective disorder which comprises administering to a human or animal subject suffering from or liable to suffer from bulimia or seasonal affective disorder an effective amount of a compound of formula (I)

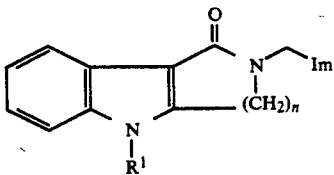

or a physiologically acceptable salt or solvate thereof, in which Im represents an imidazolyl group of formula:

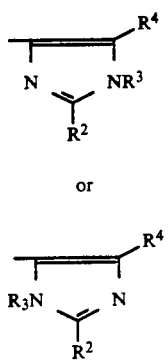

and $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl, phenyl$C_{1-3}$alkyl, phenylmethoxymethyl, phenoxyethyl, phenoxymethyl, $-CO_2R^5$, $-COR^5$, $-CONR^5R^6$ or $-SO_2R^5$ (wherein $R^5$ and $R^6$, which may be the same or different each represents a hydrogen atom, a $C_{1-6}$alkyl or $C_{3-7}$cycloalkyl group, or a phenyl or phenyl$C_{1-4}$alkyl group, in which the phenyl group is optionally substituted by one or more $C_{1-4}$alkyl, $C_{1-4}$alkoxy or hydroxy groups or halogen atoms, with the proviso that $R^5$ does not represent a hydrogen atom when $R^1$ represents a group $-CO_2R^5$ or $-SO_2R^5$);

one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$alkyl group;

and n represents 2 or 3.

2. A method according to claim 1 for the treatment of bulimia.

3. A method according to claim 2 wherein $R^1$ represents a hydrogen atom or a $C_{1-4}$alkyl, $C_{3-4}$alkenyl, $C_{3-4}$alkynyl, $C_{5-6}$cycloalkyl, $C_{5-6}$cycloalkylmethyl, phenyl$C_{1-2}$alkyl, phenylmethoxymethyl, N,N-di$C_{1-3}$alkylcarboxamido or $C_{1-3}$alkylsulphonyl group; $R^2$ represents a hydrogen atom; and $R^3$ and $R^4$ each represent a hydrogen atom or a $C_{1-3}$alkyl group.

4. A method according to claim 2 wherein n is 2.

5. A method according to claim 2 wherein $R^1$ represents a hydrogen atom or a $C_{1-4}$alkyl group; $R^2$ and $R^3$ each represent a hydrogen atom; $R^4$ represents a methyl group; and n is 2.

6. A method according to claim 2 wherein said compound of formula (I) is 2,3,4,5-tetrahydro-5-methyl-2[(5-methyl-1H-imidazol-4-yl)methyl]-1H-pyrido[4,3-b]indol-1-one or a physiologically acceptable salt or solvate thereof.

7. A method according to claim 6 wherein said compound is in the form of a hydrochloride salt.

8. A method according to claim 2 wherein said compound of formula (I) is administered orally, buccally, parenterally, rectally or transdermally or by inhalation or insufflation.

9. A method according to claim 2 wherein said compound of formula (I) is administered in a dose from 0.001 to 100 mg expressed as the weight of free base from 1 to 4 times per day.

10. A method according to claim 9 wherein said dose is from 0.1 to 20 mg.

11. A method according to claim 1 wherein the condition is seasonal affective disorder.

* * * * *